US006859965B1

United States Patent
Gourd

(10) Patent No.: US 6,859,965 B1
(45) Date of Patent: Mar. 1, 2005

(54) TENSION RELIEVING APPARATUS FOR ARMS AND NECK

(76) Inventor: Cynthia R. Gourd, 21890 E. 610 Rd., Inola, OK (US) 74036

( * ) Notice: Subject to any disclaimer, the term of this patent is extended or adjusted under 35 U.S.C. 154(b) by 0 days.

(21) Appl. No.: 10/662,740

(22) Filed: Sep. 15, 2003

(51) Int. Cl.$^7$ .............................................. A47C 17/86
(52) U.S. Cl. ................... 5/646; 5/636; 5/647; 297/393; 297/411.2
(58) Field of Search ........................... 5/636, 647, 646; 297/393, 411.2

(56) References Cited

U.S. PATENT DOCUMENTS

| | | | | | |
|---|---|---|---|---|---|
| 16,300 | A | * | 12/1856 | Wilson | 297/393 |
| 98,859 | A | * | 1/1870 | Fast | 297/393 |
| 382,949 | A | * | 5/1888 | Campbell | 297/393 |
| 673,872 | A | * | 5/1901 | Von Hillern-Flinsch | 297/391 |
| 1,463,081 | A | * | 7/1923 | Hancock | 297/393 |
| 4,560,201 | A | * | 12/1985 | Scott | 297/393 |
| 5,718,010 | A | | 2/1998 | Beier | 5/636 |
| D420,845 | S | | 2/2000 | Rumage | D6/601 |
| 6,154,905 | A | | 12/2000 | Frydman | 5/648 |
| 6,182,314 | B1 | | 2/2001 | Frydman | 5/648 |
| 6,216,298 | B1 | | 4/2001 | Oliveira | 5/636 |
| 6,327,725 | B1 | | 12/2001 | Veilleux et al. | 5/644 |
| 6,345,401 | B1 | | 2/2002 | Frydman | 5/636 |

OTHER PUBLICATIONS

Study Says Computer Workers At Risk For Stress Injuries; Occupational Hazards.
Stress In The Call Center; Utility Workers Union of America, Aug. 29, 2002.

* cited by examiner

Primary Examiner—Teri Pham Luu
(74) Attorney, Agent, or Firm—Winstead Sechrest & Minick, P.C.

(57) ABSTRACT

A tension relieving apparatus for the arms and neck which combines a generally oblong shaped pillow with first and second ends having attached connecting members which are further attached to first and second resiliently tensioned arm supporting members. The interior portion of the pillow is at least partially filled with a cushioning material conformable to the shape of a portion of the human neck. The arm supporting members allow insertion therethrough of human wrists and forearms and once so inserted generally sustain the forearms at a right angle to the upper arm. Via downward pressure on one or more of the arm members, compensating tension is applied to the neck affording the wearer simultaneous neck support and gravity negating ability to maintain one or more arms in a preferred position for typing activity.

42 Claims, 2 Drawing Sheets

TENSION RELIEVING APPARATUS FOR ARMS AND NECK

REFERENCE TO PENDING APPLICATIONS

This application is not related to any pending applications.

REFERENCE TO MICROFICHE APPENDIX

This application is not referenced in any microfiche appendix.

TECHNICAL FIELD IF THE INVENTION

In general, the present invention is generally directed towards extremity support apparatus and more particularly to a tension relieving apparatus for the arms and neck which combines a generally oblong shaped pillow, first and second resiliently tensioned arm supporting members and first and second connection members to support the rear portion of human neck and forearms.

BACKGROUND OF THE INVENTION

Call center personnel most particularly those personnel subjected to repetitive typing tasks in which the arms must be repeatedly positioned in response to consumer elicited information induces unbelievable physical stress to neck and arm portions of the human body. "Call center representatives" are women and men who assist residents, businesses and other clients in establishing or changing product orders, resolving problems, billing and a host of other customer related activities. Contrary to the popular image that suggests call center personnel are all young, single and have high turnover, more than half of those responding to the report are forty (40) years of age or older. Few of them (10%) are under 25 years of age and almost half are currently married and 44% report that they have had at least one child under the age of 18 at home living with them. The median worker has worked for their employee for 10 years and has worked in the current position for 4 years. Succinctly stated, call center representatives interacting directly with the public appear to be middle age, or rapidly approaching middle age, are under tremendous pressures to perform within deadlines suggesting a very high pressure environment and are expected to perform without making mistakes. This combined pressure obviously manifests itself in a variety of tension related maladies including, but not limited to, neck tension and arm fatigue in association with repeatedly typing data into a computer that has been structured for call center representatives/client customer interaction.

A recent survey citing stress in the call center entitled "A Report On The Worklife of Call Center Representatives In The Utility Industry" written by Stephanie Luce and Tom Juravich, documents the physical and mental stresses placed upon such workers. The Luce/Juravich report in part found that (a) almost two-thirds (61%) report that the sufficiency of their privacy is "poor" or "extremely poor", (b) almost three quarters (72%) report the pace of work has "increased" or "increased dramatically" over the past year, with 78% reporting these same changes occurring over the past two years, (c) approximately one half (48%) report that staffing is "inadequate" or "extremely inadequate", (d) the most significant factors contributing to stress include demanding customers, time pressures monitoring and pressure to complete calls, (e) one third (30%) report that stress often affects call center personnel physically and emotionally, (f) forty percent report that stress "often" or "regularly" affects their work performance, (g) workers report a variety of physical manifestations of stress including fatigue, irritability, inability to relax, headaches and backaches with almost one third (31%) report missing some work days due to stress, with a median of five days missed days per year.

Many employees spend a good portion of their day on-line, although some define that as being on the phone and others on the computer. Regardless, the median worker is on-line 84 percent of their day. As a result, 23 percent feel they never have enough time to complete other tasks, and 44 percent feel they have enough time only some of the time.

On a ten-point scale, with ten being the highest, one third of those surveyed (32 percent) rate their current stress as a ten. The overall average is 7.9. Looking at specific factors, "demanding customers" stands out clearly as the most stressful aspect of the job, with 60 percent reporting this feature as very stressful, and more than three-fourths reporting this as causing "very much" or "much" stress. The other most stressful features are "time pressures," "monitoring," and "pressure to complete calls." This reflects earlier responses noting formal quotas for the number of calls that must be made per day, but not for the amount of sales.

In terms of physical conditions, more than 40 percent of the respondents say that they often or regularly experience fatigue, irritability, inability to relax, headaches, backaches, and vision problems. Much less common are hearing and respiratory problems.

A national study by Office Organix identified computer workers at risk for stress injuries. The study concluded that over 18 million Americans are at significant risk from RSI (risk stress injuries) including carpal tunnel syndrome (CTS) and lower back injuries. Call center representatives clearly fall into this category of computer workers. In the unique situation of the call center representative, however, it is easily envisioned where the believably high pressure requirements inducing stress enhance the maladies caused by the workplace failure to provide properly sized and positioned computing furniture. By providing a unique apparatus to support the pressure areas of the human neck and to assist the call representative in minimizing the adverse consequences of gravity, the instant invention directly addresses two most significant risk factors to the typical call representative. With respect to the study conducted by Office Organix, it was found that 51% of organizations placed keyboards too high and thus contributed to neck, shoulder and wrist stress leading to CTS causes. The monitors placed too high in 65% of workers contributing to neck and shoulder stress and 47.8 cradle a foam between the head and shoulder during calls instead of using a headset. The report further found that especially dangerous over time 51.2% of respondents report when keyboarding they support their upper body by resting on their hands with a real red flag being that 59.8% suffer from wrist pain during computer work while not alleging to eliminate exposure to CTS causing events, the instant invention by affording a support mechanism which at the users direction can position the arms in a manner to minimize CTS symptoms, the instant invention greatly assists in lower the cost of business from CTS absenteeism which frequently exceeds $50,000 per year per employee when wrist surgery is required. Simply stated, though many of the costs associated with poor equipment design could be avoided with simple changes in equipment placement and employee involvement in ergonomics which changes in involvement do not appear to be in the near future. Consequently, an object of the instant invention is to provide a means by which call center/ computer workers can reduce likelihood of injury occasioned by repetitive arm/wrist movements and stress inducing cognitive factors.

BRIEF SUMMARY OF THE INVENTION

Given the deficiencies of the contemporary art, the cognitive and physical stress placed upon computer workers, most particularly those computer workers who must simultaneously interact with a customer base, it is an object of the instant invention to disclose and teach a tension relieving apparatus for the arms and neck which comprise in combination a generally oblong shaped pillow having an exterior portion, an interior section and first and second ends with each of the ends respectively attached to first and second connection members. The first and second connection members are then further attached to first and second resiliently tensioned arm supporting members.

It is a further object of the instant invention to teach the tension relieving device wherein the interior portion may further comprise a vibration and/or heat inducement means to further relieve tension and provide adjustable tensioned support to the rear portion of the human neck.

It is yet another object of the instant invention is to disclose and claim a device whereby resiliently tensioned arm supporting members may be positioned about the human wrist or forearm and thus minimize the adverse effect of gravity.

Another object of the instant invention is to teach a device in which a user may adjustably influence the amount of pressure needed to relieve neck tension and/or arm support.

A further object of the instant invention is to teach the invention's tension reducing device in which the interior portion of the pillow may be partially filled with any of a variety of cushioning materials conformable to the shape of the rear portion of the human neck.

Other objects and further scope of the applicability of the present invention will become apparent from the detailed description to follow, taken in conjunction with the accompanying drawings wherein like parts are designated by like reference numerals.

The novel configuration of the instant invention specifically directs itself towards to the alleviation/resolution of the afore noted stress and physical detriments by disclosing and claiming a tension relieving apparatus for the arms and neck comprising in combination a generally oblong shaped pillow having an exterior portion, an interior section and first and second ends with each of the ends respectively attached to the first and second connection members; and first and second resiliently tensioned arm supporting members each respectively attached to the first and second connection members.

DETAILED DESCRIPTION OF THE PREFERRED EMBODIMENT

While the making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the instant invention.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is clear that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

Figure 1:
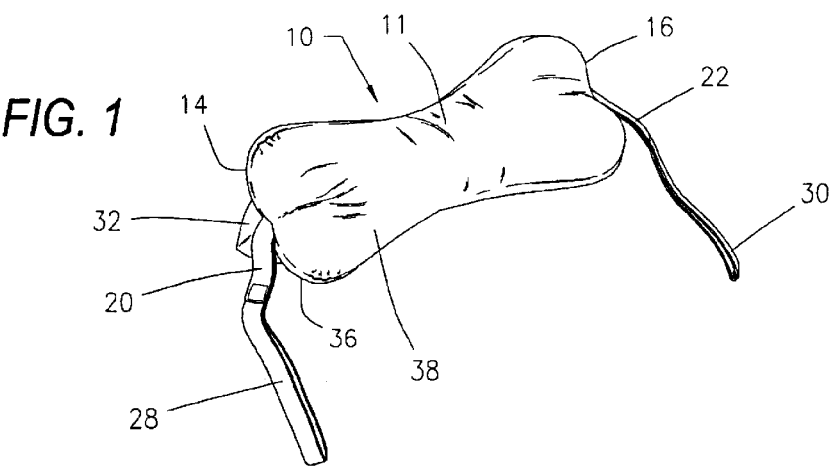
FIG. 1 is a perspective view of one embodiment of the instant invention.
Figure 2:
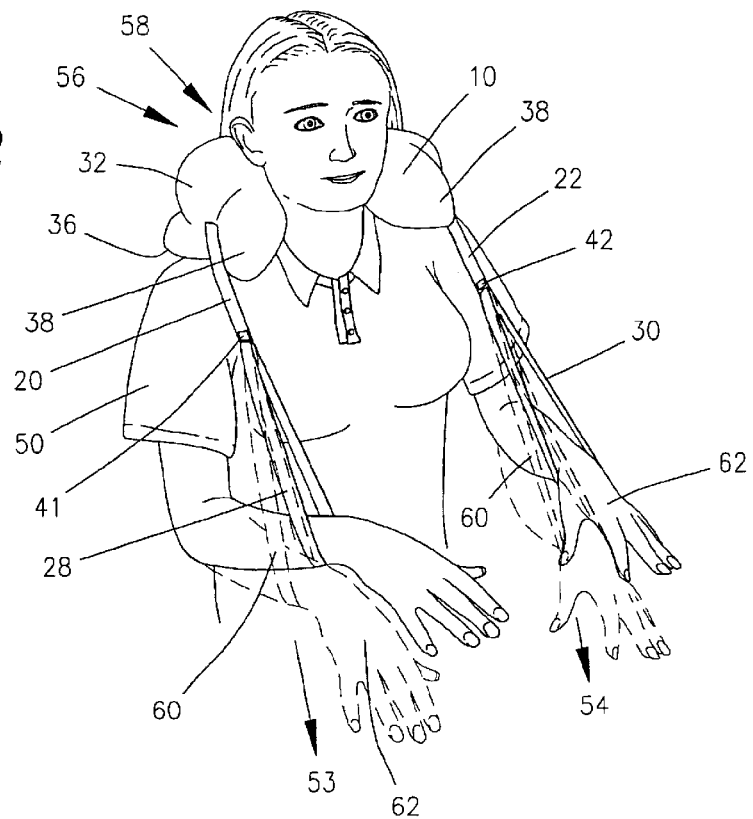
FIG. 2 is an illustration of the embodiment of FIG. 1 when positioned in accordance with the teachings of the instant invention about a human neck and forearm area.

Referring to the drawings, in which similar or corresponding parts are identified with the same reference numeral and more particularly to FIG. 1, the present invention includes a pillow designed generally at 10 having an exterior portion 11, first and second ends 14 and 16, first and second connection members 20 and 22, and first and second resiliently tensioned arm supporting members 28 and 30 which are each respectfully attached to the first and second connection members 20 and 22. The generally oblong shaped pillow of the instant invention 10 as shown in FIG. 1 is comprised of three surface areas 32, 36, 38 though it will be readily appreciated and envisioned by those skilled in the art given the disclosure and claims of the instant invention, alternative embodiments of the instant invention can be presented in a variety of form including those forms which embody a lesser or greater number of surface facings, such as pillows with pillow ends including two or more outwardly projecting lobe portions. The interior portion of the pillow 10 is not shown on FIG. 1 will be discussed in association with FIG. 3. The first and second connection members 20 and 22 are each respectfully attached to the first and second ends of the pillow 14 and 16 via a stitching or other similarly intended attachment means. Such means would include but not be limited to cloth material stitches, stitches comprised of a nylon based compound such as mono-filament, a intermediate swiveling device or clip, a belt and buckle combination or indeed hook and loop type structures typically referred to under the trademark name Velcro®. In FIG. 2, an illustration is disclosed of the embodiment of FIG. 1 when positioned in accordance with the teachings of the instant invention adorned about a human neck and forearm area(s). Turning now to FIG. 2.

In FIG. 2 it is disclosed where a person 50 has adorned or otherwise positioned the device of the instant invention 10. In so doing, exterior surface area 36 of cushion 11 has been placed about the human 50 shoulders with surface area 38 generally surrounding the rear half of the human neck. Interior surface area 32 is generally and oppositely positioned that of surface area 38. Connecting members 20 and 22 of the instant invention are further shown connected to resiliently tensioned supporting members 28 and 30 via attachment means 41 and 42, as disclosed and discussed in association with FIG. 1, to pillow first end 14 and second end 16 respectively. Attachment means 41 and 42 might very will be an intermediary swiveling device, cloth stitching or hook and loop type structure. Succinctly stated, attachment means 41 and 42 would be adequately served by any means which would reliably attach or otherwise communicate the respectful attachment of resiliently tensioned members 28 and 30, and first and second pillow ends (14, 16) to connection members 20 and 22. Also shown in FIG. 2 is the dynamic and adjustable positioning capability of the instant invention whereby when moving a human's forearms and wrists in a downward motion as indicated by lines 53 and 54, resiliently tensioned first and second members 28 and 30 expand to allow such downward movement and at the same time precipitate increasing support pressure on the rear portion of a human neck with proportionately increasing pressure indicated by lines 53 and 54 to alleviate the pressure. Consequently, the instant invention affords the user the dynamic modification of positive influencing pressure to the users neck as well as gravity defying support as provided by first and second resiliently tensioned members 28 and 30 which have been positioned about a person's arm 60 and wrists 62.

Figure 3:
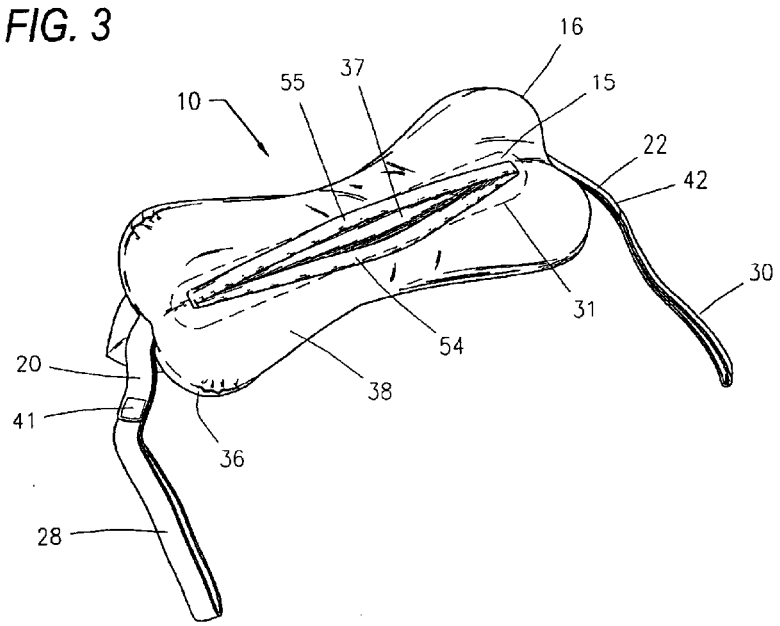
FIG. 3 is readily envisioned alternative embodiment of the instant invention wherein the internal portion of the invention has been partially vacated of cushioning material in an amount necessary to allow positioning therein of a vibrator and/or heat introduction means.

FIG. 3 is readily envisioned alternative embodiment of the instant invention wherein the internal portion of the invention has been partially vacated of cushioning material to a degree necessary to accommodate positioning therein of a vibrator and/or cold packs, and/or heat introduction means. Turning now to FIG. 3.

In FIG. 3 it is observed where the pillow of the instant invention 10 where the interior portion 15 of pillow 10 has been partially vacated indicated by hyphenated line 31. Said interior portion 15 has been partially vacated of cushioning material to allow the insertion of a heating or massaging device 37 through pocket entry illustrated as elements 54 and 55 with such device 37 being either battery or AC connected.

With respect to FIGS. 1 through 3, it is clear the resiliently tensioned supporting members 23, 30 is comprised of a loop-like structure which is adaptable to expansion and compression in response to an applied load. When the load is applied via descending motion of an arm/forearm/wrist, said resiliently tensioned members 28, 30 expand shape, and recover to their original shape when the applied load is removed. Consequently the resiliently tensioned members of the instant invention may be constructed of any such material that allows such expansion and recovery. Such materials without limitation would comprised of cloth and latex based compositions, such as bungee cord materials, or indeed any other elastomeric material. As disclosed earlier, the interior portion of the invention's pillow may be partially or completely filled with a cushion material with such cushioning material being defined without limitation as foam-based cushioning material, cloth material, down cushioning or indeed any other material that would conform generally to the rear portion of the human neck.

The deployment of the instant invention is comprised without limitation the steps of providing a generally oblong shaped pillow having an exterior portion, an interior portion and first and second ends with each of said ends respectfully attached to first and second connection members and first and second resiliently tensioned arm supporting members each respectfully attached to said first and second members. In an easily envisioned alternative embodiment resiliently tensioned arm supporting members may be attached directly to the first and second ends of the pillow via a belt and buckle combination or other similarly intended structure so as to orient the apparatus about the rear section of the human neck and above the human shoulders, then looping or otherwise positioning the first and second resiliently tensioned arm support members about the wrist or general forearm area of the human being and tensioning the pillow of the instant invention as desired by either moving the arms in a downward or upward movement.

It will of course be understood that various changes may be made in form, details, arrangement and proportions of the apparatus without departing from the scope of the invention, which generally stated consists of an apparatus capable of carrying out the objects above set forth, in the parts and combination of parts as disclosed and defined in the appended claims.

What is claimed is:

1. A tension relieving apparatus for the arms and neck comprising in combination:
   a generally oblong shaped pillow having an exterior portion, an interior section and first and second ends with each of said ends respectively attached to first and second connection members; and
   first and second resiliently tensioned arm supporting members each respectively attached to said first and second connection members.

2. The tension relieving apparatus for the arms and neck of claim 1 wherein the first and second ends of the pillow are each respectively attached to said first and second connection members via stitches comprised of a nylon based compound.

3. The tension relieving apparatus for the arms and neck of claim 1 wherein the first and second ends of the pillow are each respectively attached to said first and second connection members via cloth material stitches.

4. The tension relieving apparatus for the arms and neck of claim 1 wherein the first and second ends of the pillow are each respectively attached to said first and second connection members via hook and loop type connectors.

5. The tension relieving apparatus for the arms and neck of claim 1 wherein the first and second ends of the pillow are each respectively attached to said first and second connection members via a belt and buckle combination.

6. The tension relieving apparatus for the arms and neck of claim 1 wherein the first and second ends of the pillow are respectively attached to said first and second resiliently tensioned arm supporting members via an intermediary connecting device.

7. The tension relieving apparatus for the arms and neck of claim 1 wherein the first and second ends of the pillow are respectively attached to said first and second resiliently tensioned arm supporting members via a belt and buckle combination.

8. The tension relieving apparatus for the arms and neck of claim 1 wherein at least one of the first and second resiliently tensioned arm supporting members is a latex based continuous loop structure capable of demonstrating the physical properties of elasticity.

9. The tension relieving apparatus for the arms and neck of claim 1 wherein at least one of the first and second resiliently tensioned arm supporting members is comprised of an elastomeric material.

10. The tension relieving apparatus for the arms and neck of claim 1 wherein at least one of the first and second resiliently tensioned arm supporting members is comprised of cloth and latex based composition.

11. The tension relieving apparatus for the arms and neck of claim 1 wherein at least one of the first and second resiliently tensioned arm supporting members is comprised of material which changes shape due to an applied load and recovers its original shape when the applied load is removed.

12. The tension relieving apparatus for the arms and neck of claim 1 wherein the interior portion is at least partially filled with a foam based cushioning material.

13. The tension relieving apparatus for the arms and neck of claim 1 wherein the interior portion is at least partially filled with a down cushioning material.

14. The tension relieving apparatus for the arms and neck of claim 1 wherein the interior portion is at least partially filled with a cloth material.

15. The tension relieving apparatus for the arms and neck of claim 1 wherein the interior portion is at least partially filled with a vibrator.

16. The tension relieving apparatus for the arms and neck of claim 1 wherein the interior portion is at least partially filled with one or more cold packs.

17. The tension relieving apparatus for the arms and neck of claim 1 wherein the interior portion is at least partially filled with one or more heat packs.

18. The tension relieving apparatus for the arms and neck of claim 1 wherein the interior portion is at least partially filled with a vibrator imparting heat.

19. The combination of claim 1 wherein each said pillow end includes at least two outwardly projecting lobe portions.

20. The combination of claim 1 wherein the first and second ends are symmetric.

21. The combination of claim 1 wherein the first and second ends are identical.

22. A tension relieving apparatus for the arms and neck comprising in combination:
   a generally oblong shaped pillow having an exterior portion with at least three distinguishable exterior facing portions, an interior section and first and second ends with each of said ends respectively attached to first and second connection members and said distinguishable exterior facing portions; and
   first and second resiliently tensioned arm supporting members each respectively attached to said first and second connection members.

23. The tension relieving apparatus for the arms and neck of claim 22 wherein the first and second ends of the pillow are each respectively attached to said first and second connection members via stitches comprised of a nylon based compound.

24. The tension relieving apparatus for the arms and neck of claim 22 wherein the first and second ends of the pillow are each respectively attached to said first and second connection members via cloth material stitches.

25. The tension relieving apparatus for the arms and neck of claim 22 wherein the first and second ends of the pillow are each respectively attached to said first and second connection members via hook and loop type connectors.

26. The tension relieving apparatus for the arms and neck of claim 22 wherein the first and second ends of the pillow are each respectively attached to said first and second connection members via a belt and buckle combination.

27. The tension relieving apparatus for the arms and neck of claim 22 wherein the first and second ends of the pillow are respectively attached to said first and second resiliently tensioned arm supporting members via an intermediary connecting device.

28. The tension relieving apparatus for the arms and neck of claim 22 wherein the first and second ends of the pillow are respectively attached to said first and second resiliently tensioned arm supporting members via a belt and buckle combination.

29. The tension relieving apparatus for the arms and neck of claim 22 wherein at least one of the first and second resiliently tensioned arm supporting members is a latex based continuous loop structure capable of demonstrating the physical properties of elasticity.

30. The tension relieving apparatus for the arms and neck of claim 22 wherein at least one of the first and second resiliently tensioned arm supporting members is comprised of an elastomeric material.

31. The tension relieving apparatus for the arms and neck of claim 22 wherein at least one of the first and second resiliently tensioned arm supporting members is comprised of cloth and latex based composition.

32. The tension relieving apparatus for the arms and neck of claim 22 wherein at least one of the first and second resiliently tensioned arm supporting members is comprised of cloth and latex based composition.

33. The tension relieving apparatus for the arms and neck of claim 22 wherein at least one of the first and second resiliently tensioned arm supporting members is comprised of material which changes shape due to an applied load and recovers its original shape when the applied load is removed.

34. The tension relieving apparatus for the arms and neck of claim 22 wherein the interior portion is at least partially filled with a down cushioning material.

35. The tension relieving apparatus for the arms and neck of claim 22 wherein the interior portion is at least partially filled with a cloth material.

36. The tension relieving apparatus for the arms and neck of claim 22 wherein the interior portion is at least partially filled with a vibrator.

37. The tension relieving apparatus for the arms and neck of claim 22 wherein the interior portion is at least partially filled with one or more cold packs.

38. The tension relieving apparatus for the arms and neck of claim 22 wherein the interior portion is at least partially filled with one or more heat packs.

39. The tension relieving apparatus for the arms and neck of claim 22 wherein the interior portion is at least partially filled with a vibrator imparting heat.

40. The combination of claim 22 wherein each said pillow end includes at least two outwardly projecting lobe portions.

41. The combination of claim 22 wherein the first and second ends are symmetric.

42. The combination of claim 22 wherein the first and second ends are identical.

* * * * *

UNITED STATES PATENT AND TRADEMARK OFFICE
CERTIFICATE OF CORRECTION

PATENT NO. : 6,859,965 B1
DATED : March 1, 2005
INVENTOR(S) : Cynthia R. Gourd

It is certified that error appears in the above-identified patent and that said Letters Patent is hereby corrected as shown below:

Column 5,
Line 1, delete "will" and insert -- well --.
Line 37, delete "23" and insert -- 28 --.

Column 6,
Lines 25, 30, 34 and 38, delete "said".

Signed and Sealed this

Twenty-first Day of March, 2006

JON W. DUDAS
*Director of the United States Patent and Trademark Office*